United States Patent [19]

Arai et al.

[11] Patent Number: 5,024,816

[45] Date of Patent: Jun. 18, 1991

[54] APPARATUS FOR DETERMINING THE DEGREE OF FRESHNESS OF RAW, FROZEN AND PROCESSED FISH, POULTRY AND MEAT

[75] Inventors: Kei Arai; Minoru Ohashi, both of Tokyo; Yoshio Utsugi, Hikigun; Osamu Oka, Kawagoe; Kenichi Numazawa, Ageo; Kenji Miwa, Tokorozawa; Kenzo Sugawara, Yokohama, all of Japan

[73] Assignees: Zaidanhojin Shokuhin Sangyo Senta; Oriental Electric Company, Ltd., both of Tokyo, Japan

[21] Appl. No.: 445,924

[22] Filed: Dec. 5, 1989

Related U.S. Application Data

[63] Continuation of Ser. No. 228,571, Aug. 5, 1988, abandoned, which is a continuation of Ser. No. 874,749, Aug. 6, 1986, abandoned, which is a continuation of Ser. No. 608,972, May 10, 1984, abandoned.

[30] Foreign Application Priority Data

May 16, 1983 [JP] Japan .................................. 58-84149

[51] Int. Cl.⁵ .............................................. G01N 7/00
[52] U.S. Cl. ..................................... 422/68.1; 435/289; 426/231; 436/68; 422/80
[58] Field of Search ........................................ 422/68.1

[56] References Cited

U.S. PATENT DOCUMENTS 3,701,716 10/1972 Deuringer ............................. 422/68
4,097,921 6/1978 Raffaele ................................. 436/68

Primary Examiner—Robert J. Warden
Assistant Examiner—Lyle Alfandary-Alexander
Attorney, Agent, or Firm—Oblon, Spivak, McClelland, Maier & Neustadt

[57] ABSTRACT

Disclosed is a method for determining the degree of freshness of such raw, frozen and processed perishable foodstuffs as meat, poultry and fish and an instrument therefor. The degree of freshness can be easily determined by the method of the present invention in shorter periods of time than by the conventional methods.

The method of this invention comprises determining the amount of certain decomposition products of adenosine triphosphate such as hypoxanthine, inosine and inosinic acid by measuring the consumption of dissolved oxygen while each compound is subjected to action by certain enzymes, i.e., hypoxanthine by xanthine oxidase, inosine by nucleoside phosphorylase and inosinic acid by alkaline phosphatase, nucleoside phosphorylase and xanthine oxidase.

1 Claim, 12 Drawing Sheets

```
          No.i
   DATA     :    %
   Hx    2.82 : 32.2
   HxR   2.85 : 32.6
   IMP   3.08   35.2
               8.75
```

APPARATUS FOR DETERMINING THE DEGREE OF FRESHNESS OF RAW, FROZEN AND PROCESSED FISH, POULTRY AND MEAT

This application is a continuation of application Ser. No. 07/228,571, filed on Aug. 5, 1988, now abandoned, which is a continuation of application Ser. No. 874,749, filed on Aug. 6, 1986, now abandoned; which is a continuation of application Ser. No. 608,972, filed on May 10, 1984 (abandoned).

BACKGROUND OF THE INVENTION

1. Field of the Invention

The fields to which this invention applies include the agricultural, marine product and food processing industries.

2. Description of the Prior Art

Perishable foodstuffs such as raw, frozen and canned meat, poultry and fish are an important part of the diets of most people and of the international trade of many nations. The degree of freshness of these foods affects their marketability and edibility. Spoiled foods present the risk of illness.

Fish, for example, lose its freshness more quickly than meat. Further, the quality of canned salmon, tuna, crab and the like depends on the freshness of the fish or shellfish used for processing. The quality of freshness can seldom be visually determined because fish is often sold in frozen or processed form.

Perishable foodstuffs imported into the United States, for example, are subject to stringent quality inspection by the Food and Drug Administration. It has been found that up to 30% of canned fish exported from Japn, for example, is spoiled, resulting in the necessity of disposing of the spoiled products.

From the standpoint of consumer protection and food hygiene, detailed studies have been made in Japan of methods for determining the degree of freshness of fish. Based on the fact that the compounds derived from necleic acid-related compounds contained in a fish extract solution undergoes change as shown in the following equation (1), the studies have established a relationship between each compound ratio and the freshness of fish:

$$ATP \rightarrow ADP \rightarrow AMP \rightarrow IMP \rightarrow HxR \rightarrow Hx \qquad (1)$$

For example, Uchiyama et al. (Bulletin of the Japanese Society of Scientific Fisheries, Vol. 36, 977 (1970)) made an analysis of the above compounds by using liquid chromatography to show that a deterioration in freshness can be detected from an increase in the value of K as in equation (2)

Value of $K =$ \qquad (2)

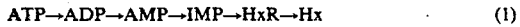

$$\frac{H \times R + Hx}{(ATP + ADP + AMP + IMP + HxR + Hx)} \times 100(\%)$$

Fujii et al. (Ibid., Vol. 39, 69-84 (1973)) determined each amount of IMP, HxR and Hx by using an enzymatic method to estimate the degree of freshness depending on the type of the fish from the numerical values shown in formulas (3) to (5):

$$IMP\ ratio = \frac{IMP}{(IMP + HxR + Hx)} \times 100(\%) \qquad (3)$$

$$HxR\ ratio = \frac{HxR}{(IMP + HxR + Hx)} \times 100(\%) \qquad (4)$$

$$Hx\ ratio = \frac{Hx}{(IMP + HxR + Hx)} \times 100(\%) \qquad (5)$$

The IMP ratio exhibits a higher value when the degree of freshness is high and decreases as the degree of freshness decreases. Canned tuna having an IMP ratio of 40% or higher can be judged as having been processed from raw tuna having a high degree of freshness.

The compounds ATP, ADP, AMP, IMP and Hx shown in the above equations (1) to (5) represent the following:
- ATP: adenosine triphosphate
- ADP: adenosine diphosphate
- AMP: adenosine monophosphate.
- IMP: inosinic acid
- HxR: inosine
- Hx: hypoxanthine The above methods for determining the degree of freshness of fish are also effective as measures for determining the degree of freshness of poultry such as chicken (see Numata et al., Journal of Japanese Society of Food Science and Technology, Vol. 28, 542-(1981); and Kitada et al., Ibid., Vol. 30, No. 3, 151-154 (1983)).

Both of the above methods, however, need to be carried out in specially equipped laboratories by skilled personnel.

SUMMARY OF THE INVENTION

An object of this invention is to provide a simpler, more rapid, more economical method of determining the degree of freshness of perishable foodstuffs than the conventional methods described above.

Another object of this invention is to provide a measuring device and reagents, which are necessary for the practice of this invention, for the practice of the method of this invention and to promote rationalization in the storage, processing, shipping and retailing and the like of such foodstuffs as raw, frozen and processed meat, poultry and fish by wider use of the above measuring device and reagents.

Another object of this invention is to provide a method for determining the degree of freshness of the above foodstuffs and a measuring device and reagents therefor which are capable of solving the technical problems described below in the conventional methods described above.

The conventional chromatographic method has the following disadvantages:

1) An expensive liquid chromatography and technicians skilled in operating such equipment are necessary.
2) The separation procedure take about 3 hours on average and, further, column regeneration takes even longer.
3) It is difficult for this method to separate inosine (HxR) from hypoxanthine (Hx).

The conventional enzymatic method has the following disadvantages:

1) An expensive ultraviolet spectropometer is necessary.
2) Two separate and expensive enzymes are necessary in order to conduct a blank measurement.
3) The enzymatic reaction takes about 40 minutes.

4) Corrosive perchloric acid has to be used as the extractant because trichloroacetic acid having ultraviolet absorbing properties cannot be used as the extractant.

5) The entract solution must be clarified by centrifuging twice and this takes about one hour.

The present invention makes it possible to overcome the above problems in the prior art by bioelectrochemical means by providing a simple and economical method- for determining the degree of freshness of perishable foodstuffs by use of a simple measuring device and by the effective use of oxygen. In other words, the present invention provides a method for determining said degree of freshness from the values obtained by a composition analysis of certain ATP decomposition products, which method comprises determining the amount of hypoxanthine (Hx) from the consumption of dissolved oxygen due to the oxidation of xanthine oxidase (XO); determining the amount of inosine (HxR) from the consumption of dissolved oxygen due to the combined action of nucleoside phosphorylase (NP) and xanthine oxidase (XO); and determining the amount of inosinic acid (IMP) from the consumption of dissolved oxygen due to the combined action of alkaline phosphatase (AP), nucleoside phosphorylase (NP) and xanthine oxidase (XO), by use of an oxygen sensor; and provides an instrument for determining said degree of freshness, which instrument comprises a reaction cell provided with a dissolved oxygen sensor, an amplifier for sensing signals and a recording device. The instrument and reagents required in the practice of the present invention comprise 1) a measuring device for determining dissolved oxygen (hereinafter referred to as a DO measuring device);
2) a reaction cell provided with a DO sensor; and
3) extractants, enzymes and pH buffer solutions.

DETAILED DESCRIPTION OF THE PREFERRED EMBODIMENTS

Figure 1:
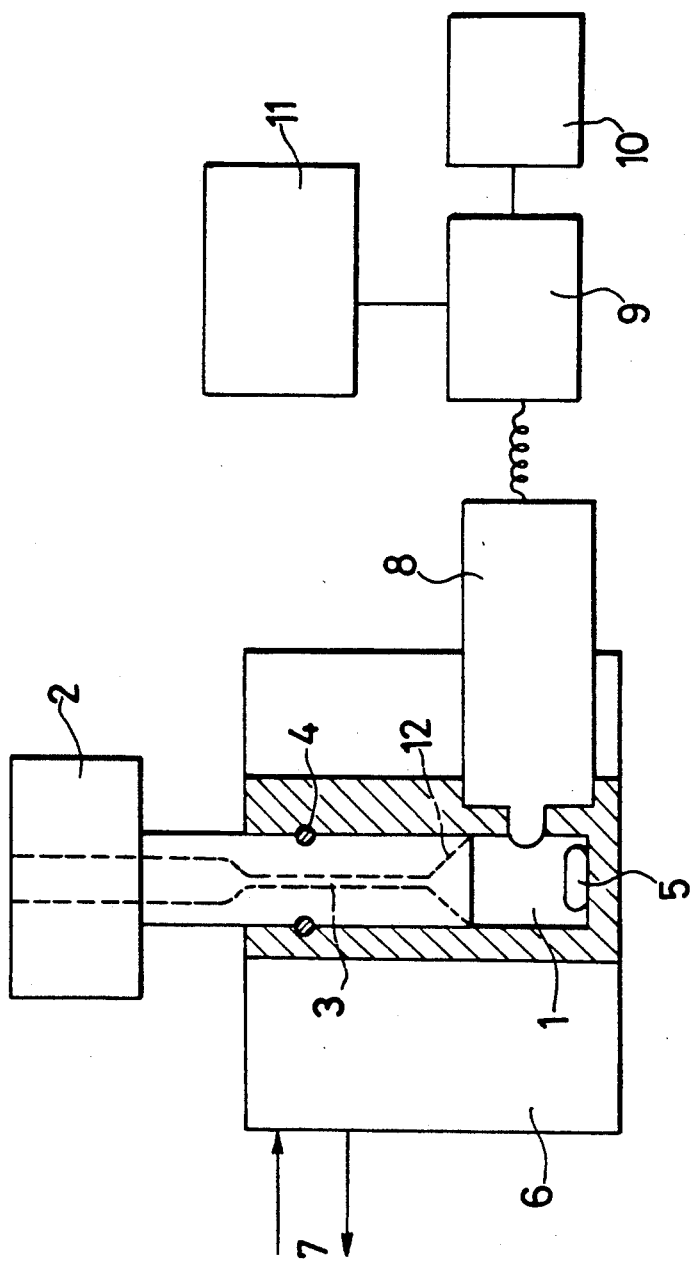
FIG. 1 is a flow sheet of an instrument used in the present invention.

The present invention will now be explained in greater detail with reference to the drawings described above. FIG. 1 shows an example of the instrument used in the present invention. In FIG. 1, 1 is a reaction cell, the volume of which is preferably of from 1 to 2 ml to save the amount of reagents used. 2 is a stopper in the reaction cell, said stopper being provided with a capillary 3 used for liquid injection in the center thereof, said capillary having, for example, a diameter of about 1 mm. 4 is an o-ring for hermetic sealing, 5 a stirrer bar of a magnetic stirrer, and 6 a jacket for temperature control, through which exterior isothermal water 7 is circulated. The shape of the reaction cell is not specifically limited, but should be so constructed as to be convenient for injection of the reagents, to make possible reaction temperature control and agitation of the reaction mixture for mixing and to prevent oxygen from the outside from being dissolved in the reaction mixture during the agitation thereof.

The dissolved oxygen (DO) measuring device used may be of any type using an oxygen sensor of, for example, a polarographic system, a galvanic cell system, an oxygen ballanced system or the like 9 is an amplifier. A recorder 10 for DO may be any commercially available mV recorder, and preferably should be able to record at a speed of a unit per minute with a full range of 10 mV. 11 is a computer. The instrument used in the present invention should be small and light enough for use on site in a processing plant or other location, in addition to in a laboratory.

The reagents used include enzymes which make it possible to conduct the reactions shown in equation (6) quickly.

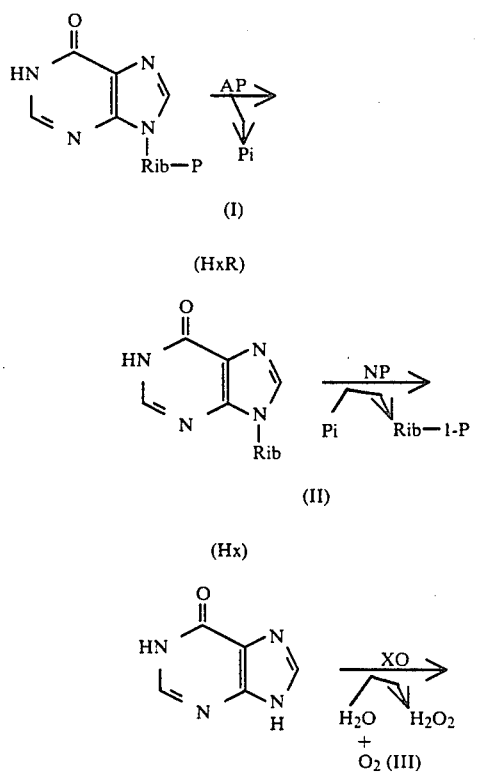

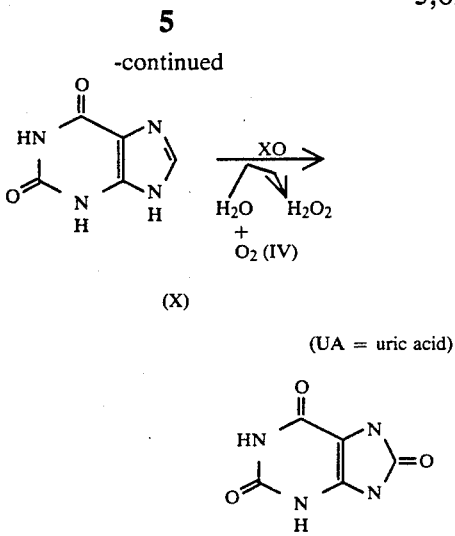

(UA = uric acid)

In equation (6), AP, NP and XO indicate alkaline phosphatase, nucleoside phosphorylase, and xanthine oxidase, respectively. The AP, NP and XO to be used should be commercially available and active stock.

Figure 2:
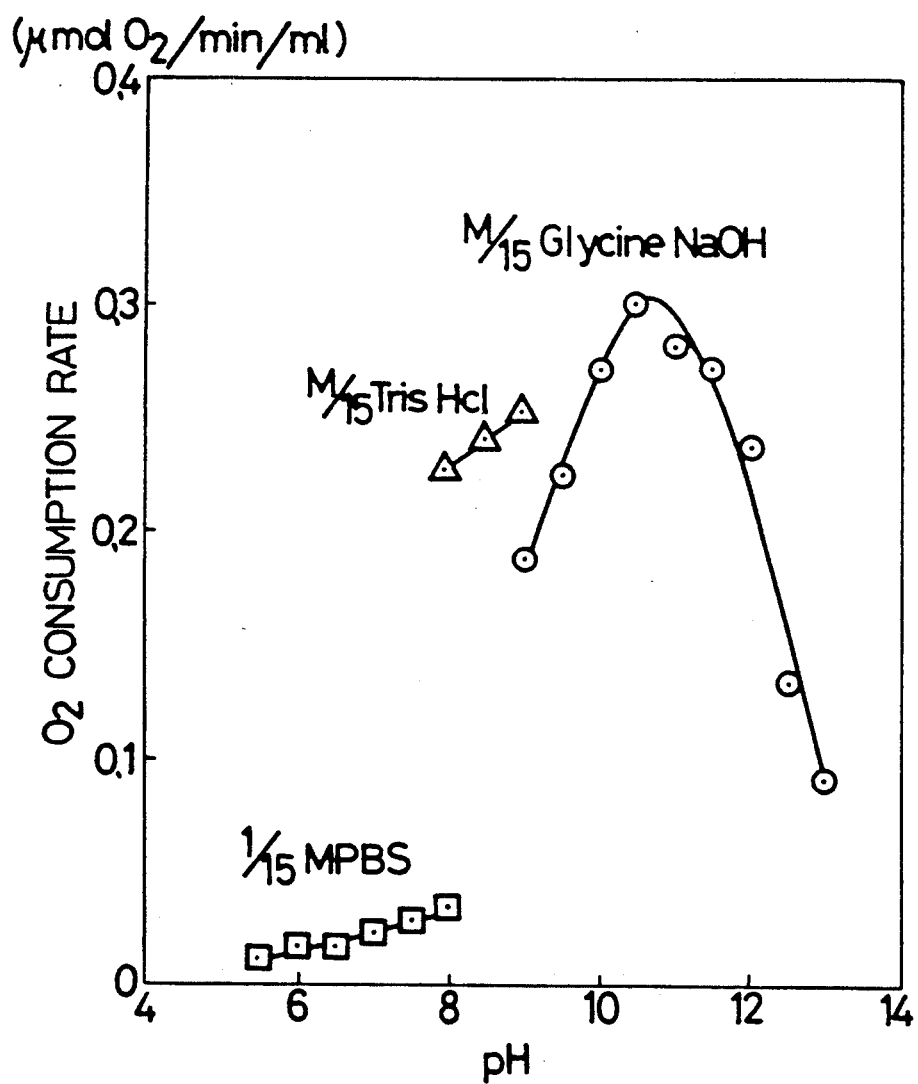
FIG. 2 is a pH-based alkaline phosphatase activity curve.
Figure 3:
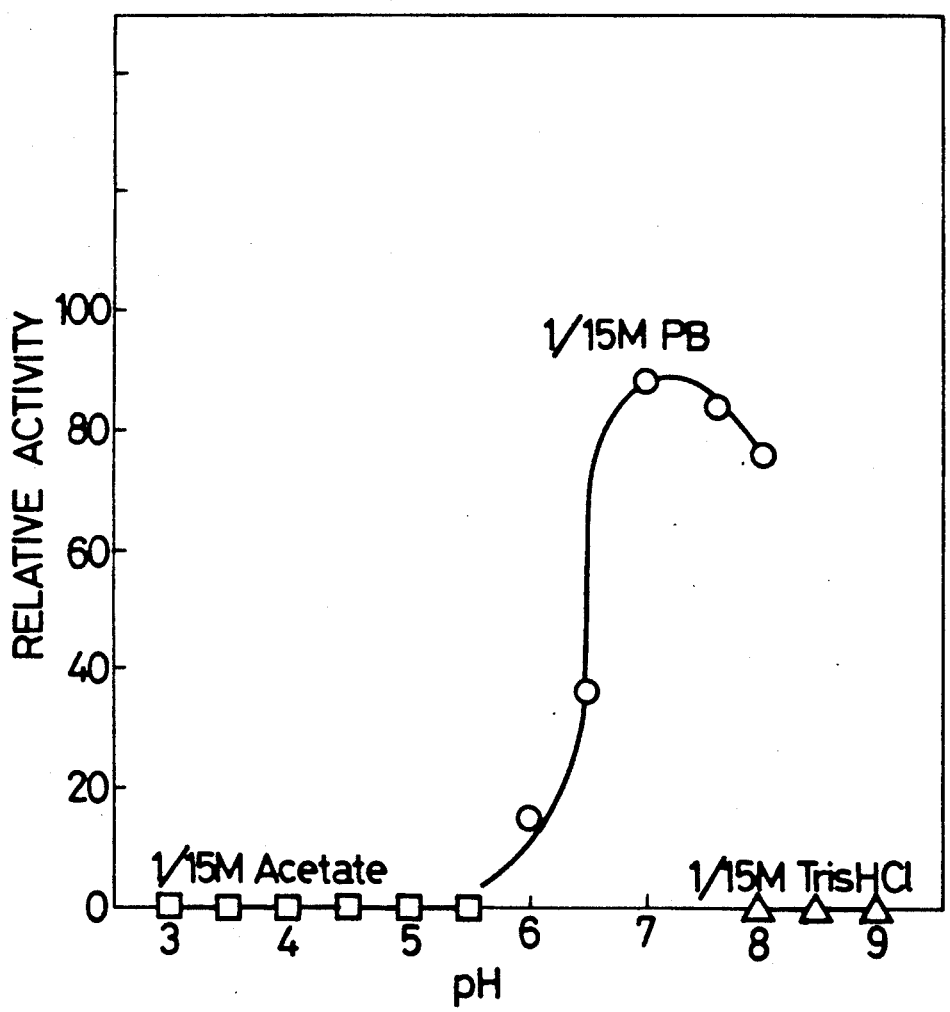
FIG. 3 is a pH-based nucleoside phosphorylase activity curve.
Figure 4:
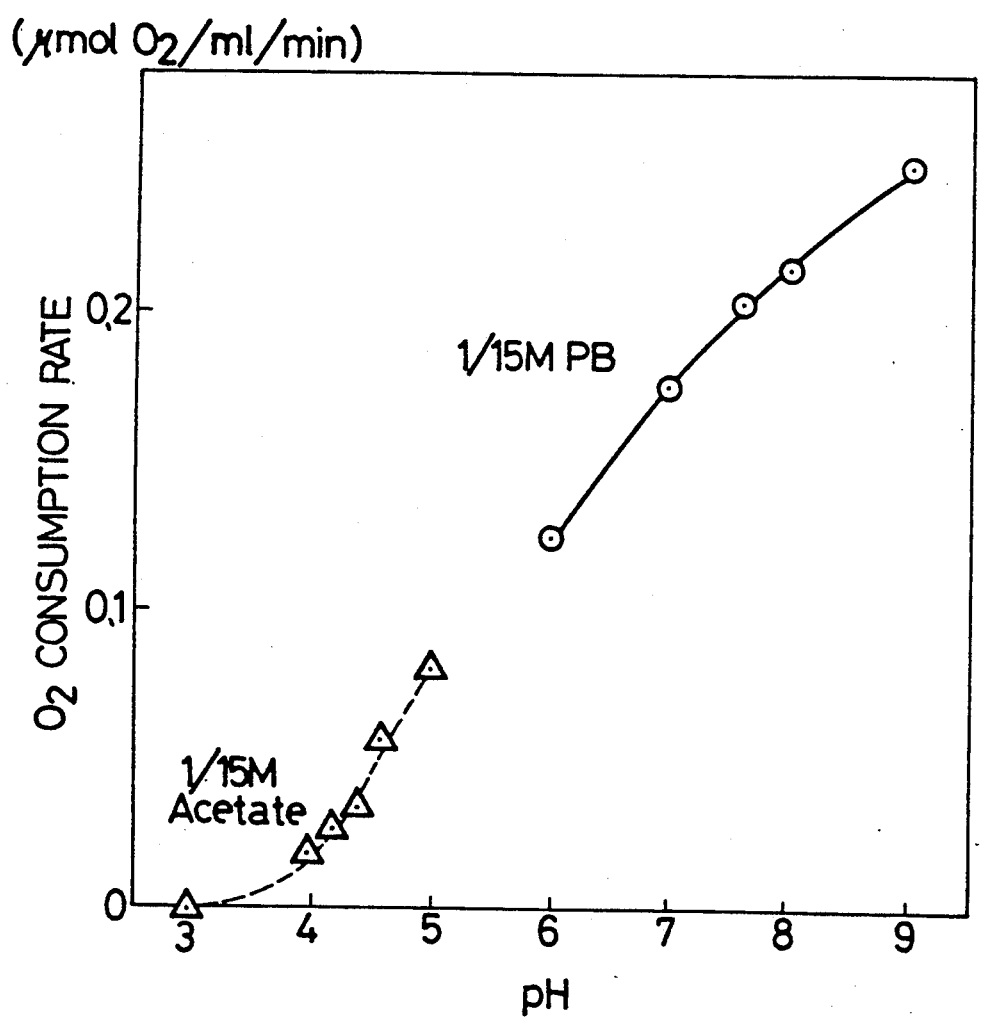
FIG. 4 is a pH-based xanthine oxidase activity curve.

As shown in FIG. 2, since AP exhibits a maximum activity at about pH 10.5, 1/15M.glycine-NaOH buffer solution (G.B.), for example, should be used as a pH buffer solution to which AP is applied. Since NP and XO exhibit: a maximum activity in the neighbourhood of the neutral point, 1/15M phosphate buffer solution (P.B.) should be used as the buffer solutions as shown in FIGS. 3 and 4 for NP and XO, respectively.

Extraction of a compound from a specimen may be effected with parchloric acid (PCA), but preferably with trichloroacetic acid (TCA) because of safety in handling and because no precipitation is formed on. neutralization. However, TCA cannot be used in determining freshness through use of UV as in the method of Fujii et al. because TCA has UV-absorbing properties. However, TCA may be freely used in the method of the present invention, because determining freshness according to the method of the present invention is carried out electrochemically.

Since the sensing device in the method of the present invention is based on oxygen consumption which takes place due to the oxidation of XO as shown at steps (III) and (IV) in equation (6), it is necessary for the reaction mixture to be aerated in advance so that oxygen may be sufficiently dissolved therein.

Figure 5:
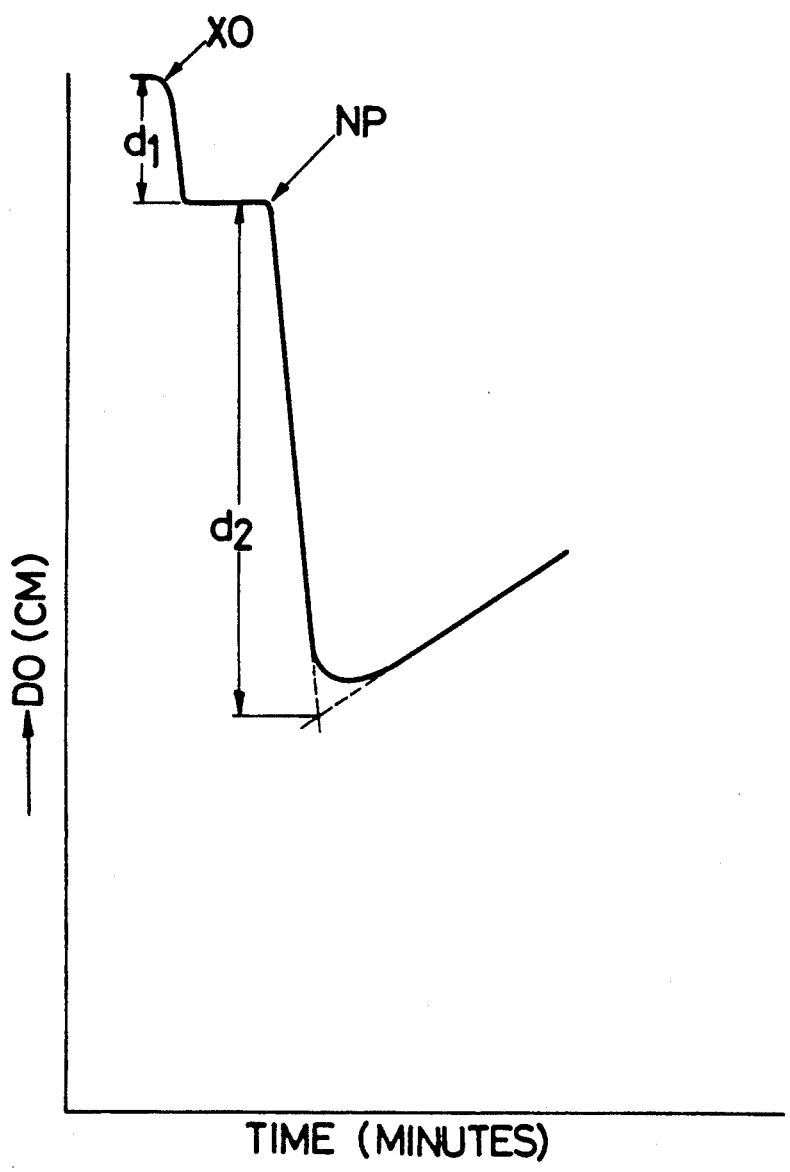
FIG. 5 is a curve showing phenomena disturbed by catalase.

As shown at steps (III) and (IV) in equation (6), hydrogen peroxide is formed concurrently with oxygen consumption. Therefore, if a catalase is present in the test solution or in the enzyme, as shown in FIG. 5, oxygen is generated from hydrogen peroxide with the result that DO increases to disturb proper measurement. Thus, the enzymes used in the present invention need to be free of catalase However, oxygen generation due to the presence of catalase in a small amount may be corrected by extrapolation as shown in FIG. 5.

Air bubbles remaining in the reaction cell are also responsible for an increase in DO. Care must be taken that the reaction cell is completely filled with the buffer solution and that no air bubbles are entrained on injection of the sample or enzyme. As shown in FIG. 1, a taper 12 at the bottom of the stopper 2 for the reaction cell should have, for convenience, a slope greater than 45° so that no air bubbles may remain therein.

The output current of the DO sensor used in the present invention is very sensitive to temperature and the temperature of the reaction mixture must be kept at a constant level. The reaction temperature should be kept preferably at about 37° C. The reaction mixture saturated with air at that temperature contains oxygen dissolved therein in an amount of about 0.2 $\mu$mol/ml. The amount of DO may be obtained from a numerical table of the amount of oxygen dissolved in water under saturation (see, for example, "Optimum Instrumentation and Control in Fermentation Processes", Table 1, page 206, published by Science Forum Co., Ltd.).

Enzymes used for the determination of Hx, HxR and IMP and preferable reaction conditions thereof are shown in Table 1 below.

TABLE 1

| | Enzymes Used and Reaction Conditions Thereof | | |
|---|---|---|---|
| Compound to be determined | Hypoxanthine (Hx) | Inosine (HxR) | Inosinic acid (IMP) |
| Enzyme to be used | XO 4 U/ml 20 $\mu$l | NP 100 U/ml 8 $\mu$l<br>XO 4 U/ml 20 $\mu$l | AP 350 U/ml 20 $\mu$l<br>NP 100 U/ml 8 $\mu$l<br>XO 4 U/ml 20 $\mu$l |
| Buffer solution | 1/15 phosphate buffer solution (pH 7.6) | 1/15 M phosphate buffer solution (pH 7.6) | 1/15 M glycine - NaOH buffer solution (pH 10.5)<br>1/15 M phosphate buffer solution (pH 7.6) |
| Reaction temperature | 37° C. | 37° C. | 37° C. |

Figure 6:
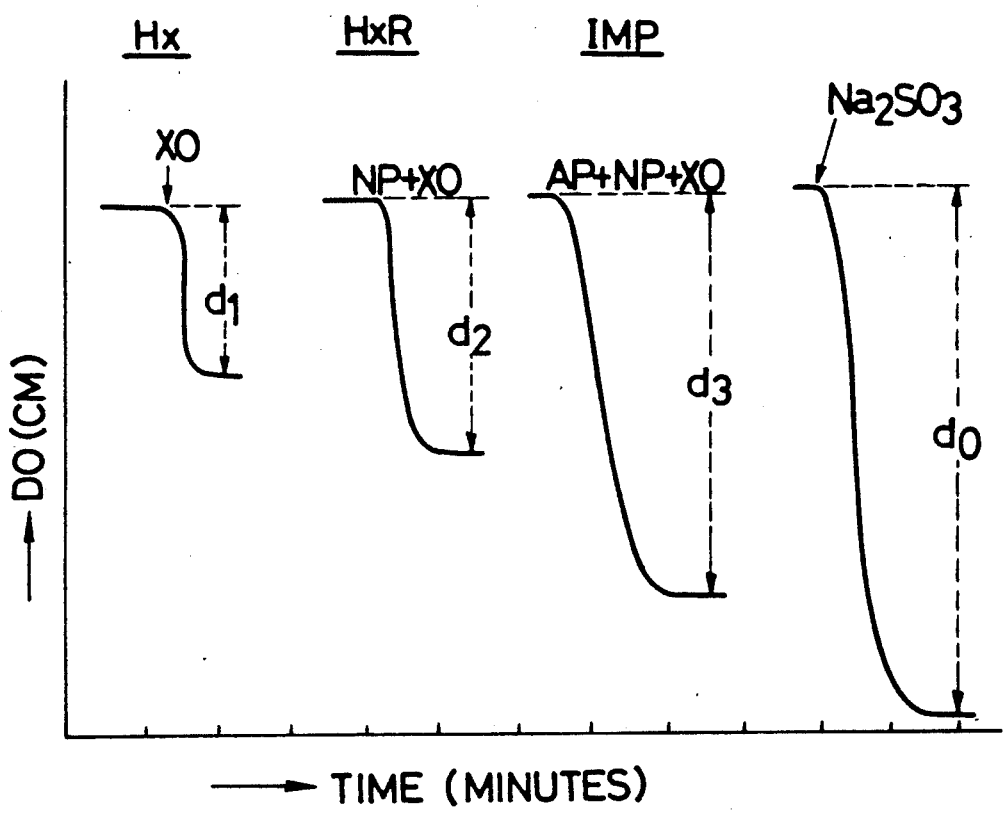
FIG. 6 is a curve showing DO consumption.
Figure 7:
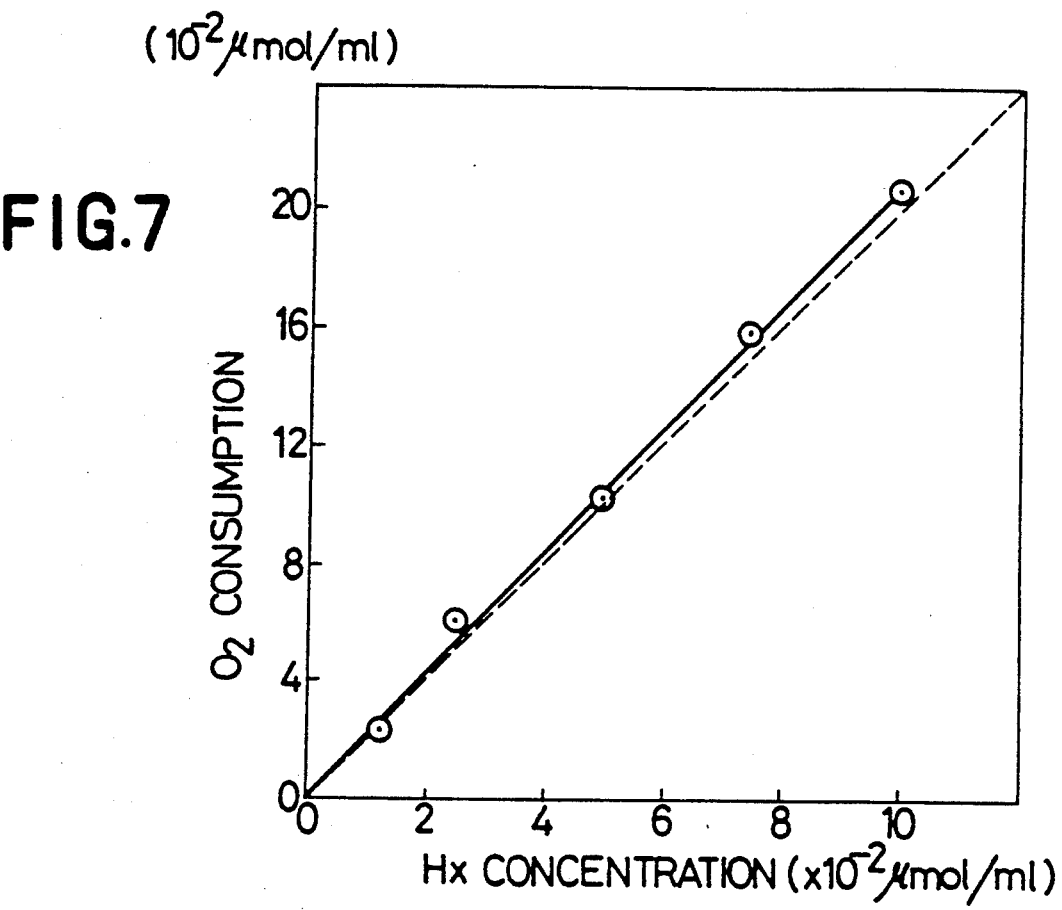
FIGS. 7, 8 and 9 are calibration curves for Hx, HxR and IMP, respectively.
Figure 8:
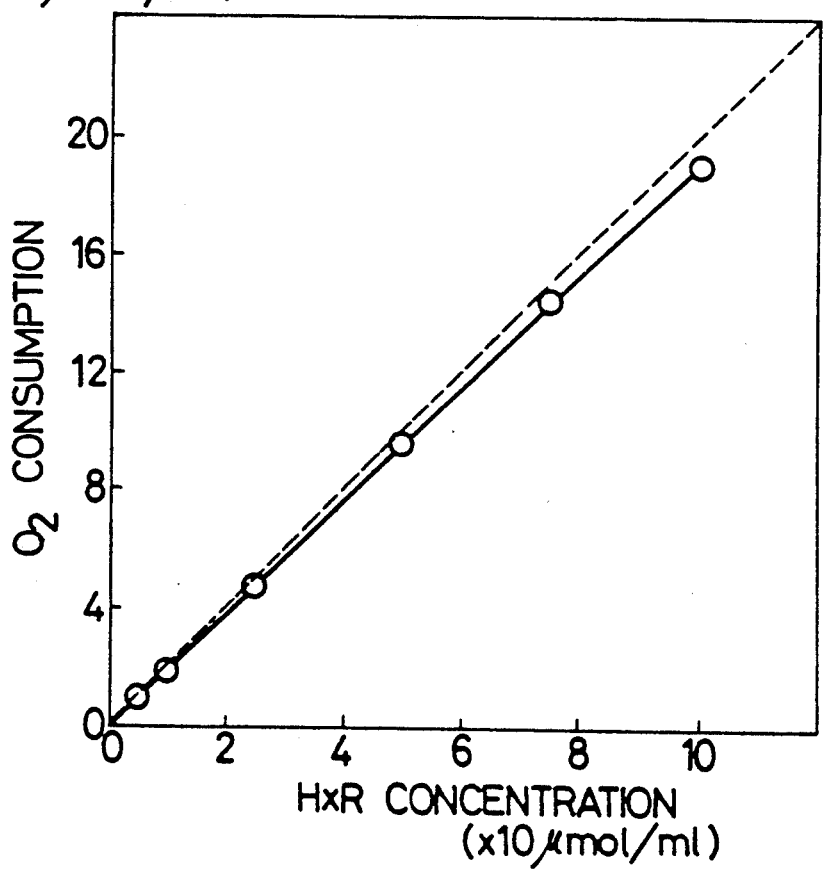
Figure 9:
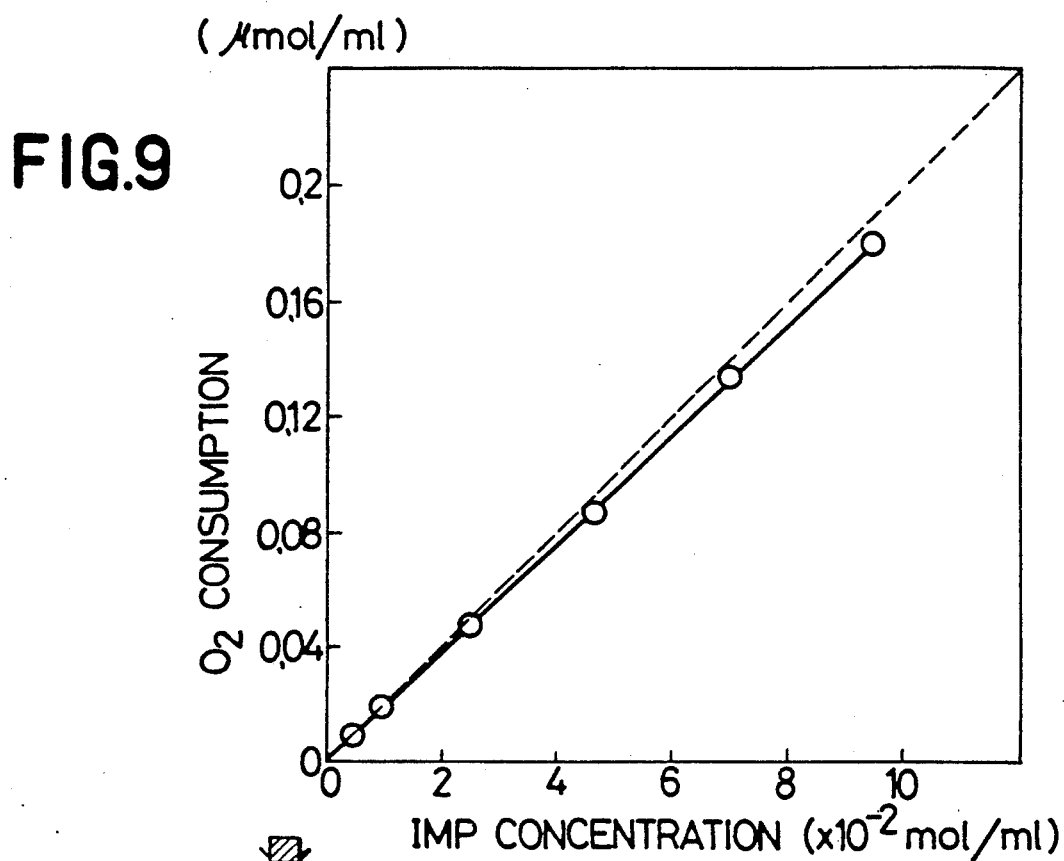

In starting the reaction, the cell is filled with a phosphate buffer solution, and then sealed by a stopper, following which a sample is injected through a capillary of the stopper. A sample for IMP, obtained separately by a pre-reaction by using a glycine-NaOH buffer solution and AP, is injected thereinto. As soon as the enzyme is injected the amount of DO rapidly decreases a curve showing DO consumption is recorded for about one minute on a recorder as shown in FIG. 6. The consumption (do) from DO saturation and DO zero is measured, and the length of do corresponds to 0.214 $\mu$mol $O_2$/ml at 37° C. Thus, the amounts of oxygen consumed can be determined from $d_1$, $d_2$ and $d_3$ as shown in FIG. 6. Calibration curves showing the relationship between concentrations and oxygen consumption of samples of Hx, HxR and IMP are shown in FIGS. 7, 8 and 9, respectively. This shows that the reactions shown in equation (6) proceed quantitatively and rapidly. Two moles of oxygen are absorbed per mole of compound, and the water saturated with air contains oxygen at a concentration of about 0.2 $\mu$mol/ml. Therefore, samples should be prepared in such a way that the total moles of the compound to be determined remain below 0.1 μmol on reaction.

Figure 10:
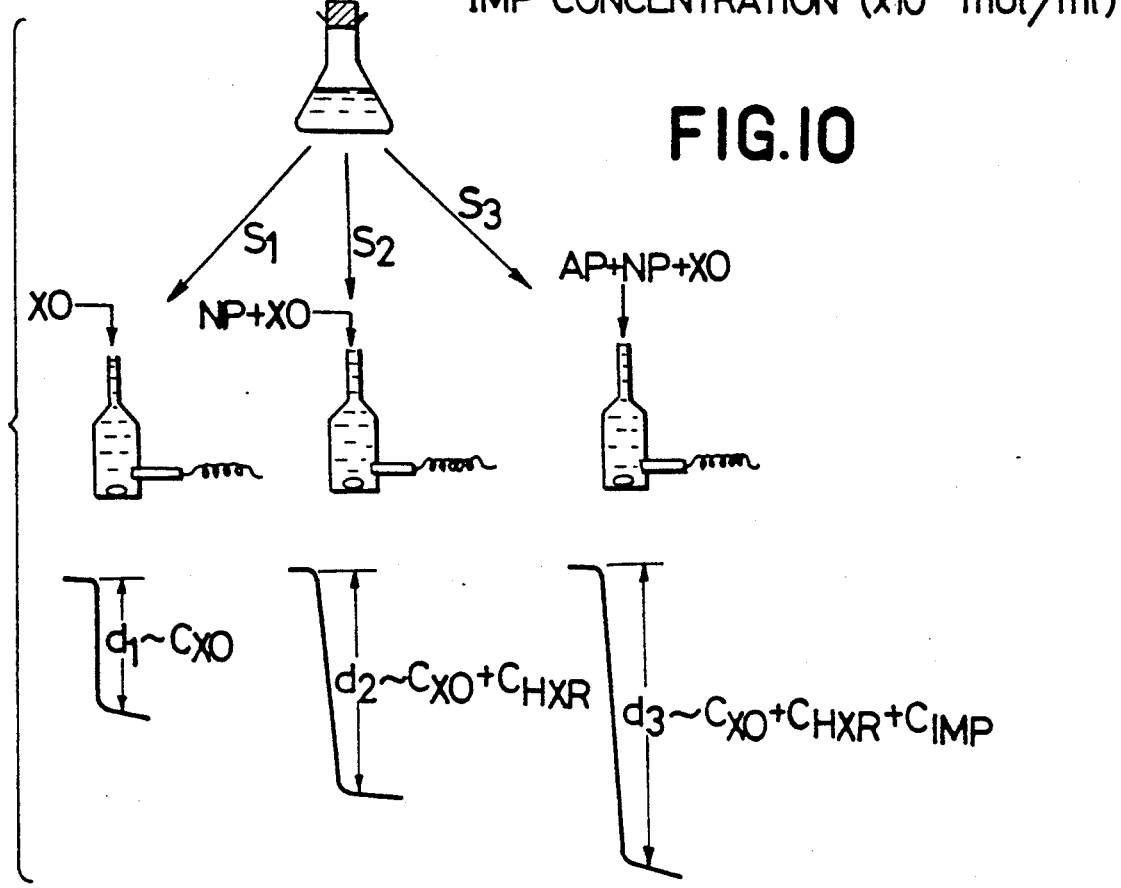
FIGS. 10, 11 and 12 are curves showing DO consumption according to the first, second and third methods for determining respectively

According to a first method of determining freshness with an actual sample, as shown in FIG. 10, the sample is divided equally into samples $S_1$, $S_2$ and $S_3$, and the DO consumption in each step, which is obtained in the same manner for each sample, may be combined to obtain each compound ratio. In a sample $S_1$, decrease in DO concentration i.e. DO consumption due to conducting the reactions at steps (III) and (IV) in equation (6) is detected, and hypoxanthine (Hx) is detected due to the reactions, because xanthine (x) is usually absent in a meat extract solution. The consumption recorded is represented as $d_1$. In a sample $S_2$, consumption ($d_2$) corresponding to the combined amount of inosine (HxR) and Hx is obtained by conducting the reactions at steps (II), (III) and (IV) in equation (6). In a sample $S_3$, where AP is used in the alkaline range followed by the use of NP and XO at the neutral point, consumption ($d_3$) corresponding to the combined amount of inosinic acid (IMP), HxR and Hx is obtained. Consequently, the amount of HxR is determined as $d_2-d_1$, while that of IMP is determined as $d_3-d_2$. Therefore, the present invention makes it possible, to determine very easily the IMP, HxR and Hx ratios from equations (7), (8) and (9), respectively, below.

$$IMP\ ratio = \frac{d_3-d_2}{d_3} \times 100\% \tag{7}$$

$$HxR\ ratio = \frac{d_2-d_1}{d_3} \times 100\% \tag{8}$$

$$Hx\ ratio = \frac{d_1}{d_3} \times 100\% \tag{9}$$

Figure 11A:
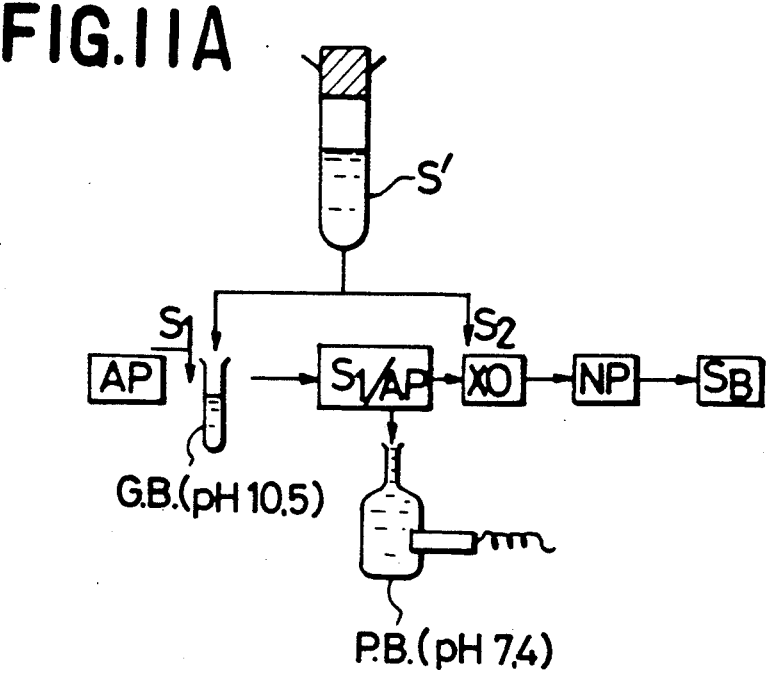
Figure 11B:
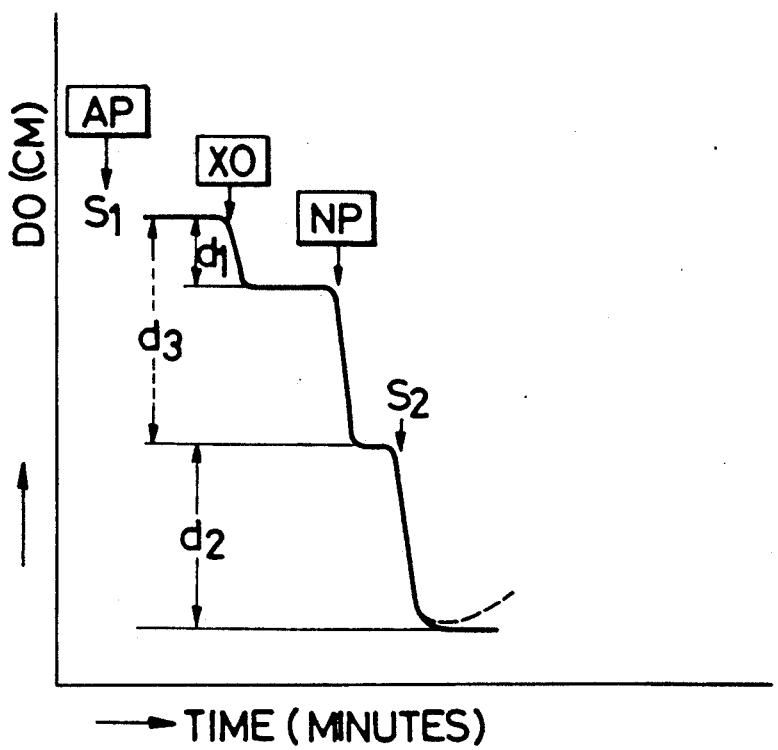

In order to simplify procedures and save samples and enzymes, a second method for determining freshness may be carried out as follows: A sample $S_1$, AP and G.B. are charged into a reaction cell to effect a prereaction for 3 minutes, and P.B., in such an amount as to be slightly greater than the volume of the reaction cell so that the liquid mixture penetrating into the capillary in the stopper provides a water sealing effect and contributes to prevent oxygen from the outside from entering thereinto, is then added to be sealed by a stopper. The amount of the liquid mixture forced into the capillary due to the injection of enzymes and samples is in such a trace amount as to be negligible compared with the whole capacity of the reaction cell. XO is then injected into the reaction cell, following which the cessation of DO consumption is first confirmed from the recorder; immediately thereafter NP is injected to record the consumption of DO in a second step, and finally a sample $S_2$, which is not subjected to pre-reaction, is injected. Thus, a consumption curve with 3 steps is obtained, as shown in FIG. 11, in which $d_1$, $d_2$ and $d_3$ correspond to the amounts of Hx, HxR+Hx and IMP+HxR+Hx, respectively. Since the final reaction takes place while the pH of the reaction mixture is controlled at a neutral level, as is apparent from FIG. 2, AP does not act, while NP and XO act.

Figures 12A, 12B:
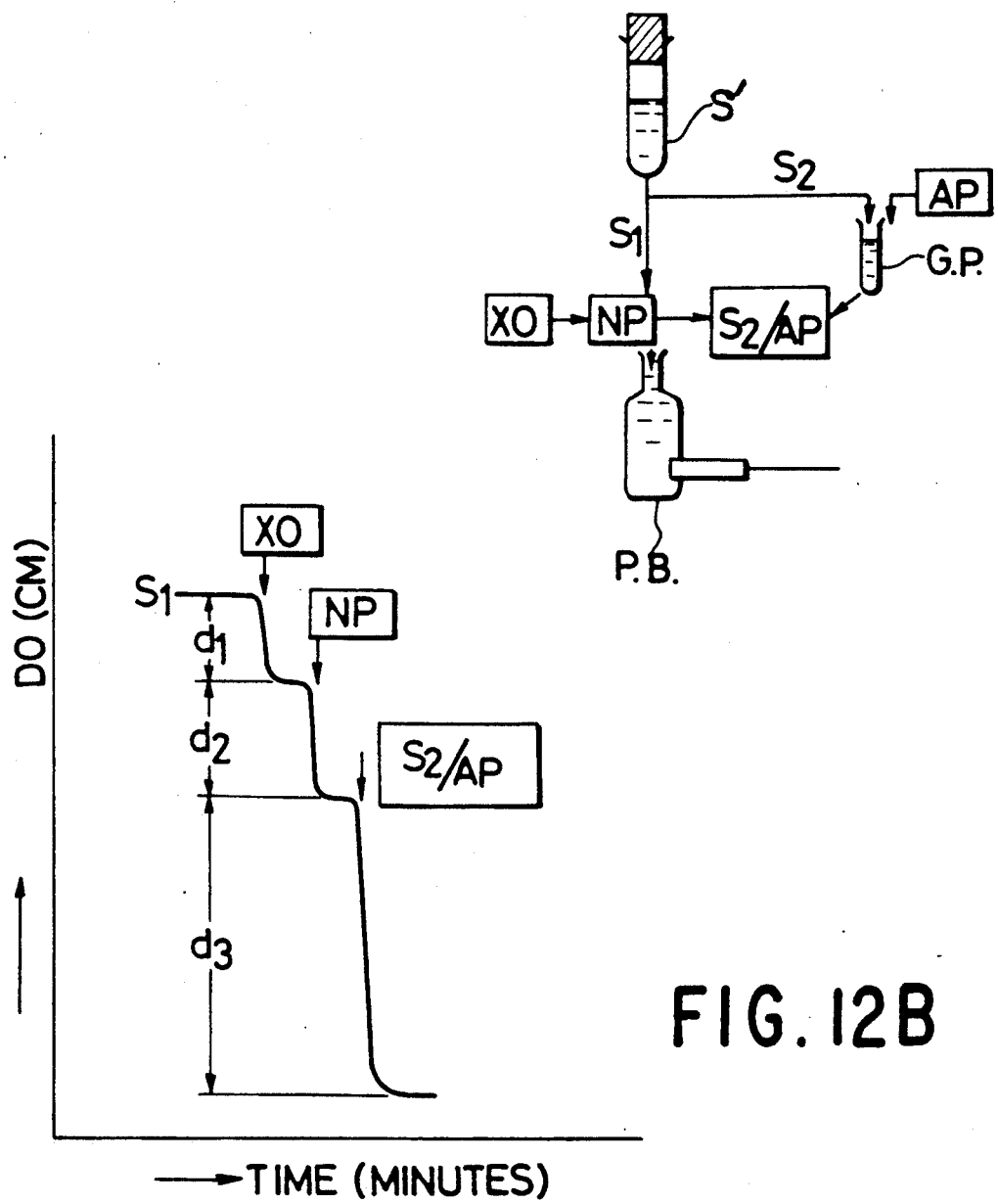

A third method for determining freshness is a modification of the second method. According to this third method, the reaction cell is filled with P.B. to be sealed by a stopper, and a non-treated sample $S_1$ is injected. XO and NP are reacted in that order, while an AP Treatment of another sample $S_2$ is carried out in a separate vessel. The pre-treated sample $S_2$ is injected into the reaction cell. A decrease curve with 3 steps is shown in FIG. 12 in which $d_1$, $d_2$ and $d_3$ correspond to Hx, HxR and IMP; HxR+Hx, respectively. According to this third method, the AP reaction is not carried out in the reaction cell, with the result that the amount of AP used increases to some extent compared with the second method. However, this third method has the advantage that the reactions as a whole can be completed in a very short period of time, because the sample $S_2$ can be subjected to the AP reaction at the same time as the XO reaction and the NP reaction of the sample $S_1$.

According to the second and third methods, the XO and NP, which have been injected once, continue to react throughout, as a result of which the amount of XO used can be reduced to one third that used in the first method, and the amount of NP used can be reduced to half that used in the first method. The second and third methods are therefore very economical. The order and combinations of the reactions, however, may be modified.

The reaction of each step as described above can be completed in 1 to 2 minutes, and the reactions of all three steps can be completed in about 5 minutes. Therefore, the method of the present invention is obviously a very rapid method compared to the conventional methods which normally take several hours or several tens of minutes at the minimum. In addition, the method of the present invention uses a much smaller amount of reaction mixture compared with the conventional methods.

Basic research conducted by Uchiyama et al. and Fujii et al. as described above teaches that there is no need to determine the absolute concentration of each compound, but that it is sufficient to determine only the concentration ratio, in evaluating the degree of freshness. Therefore, it is sufficient to determine the rate of change obtained by recording the change in the output current of the DO sensor, said change being proportionate to the concentration of each compound. However, in the case where the concentration itself must be determined, the method the present invention has the advantage that such determination may be made by use of air saturated water, instead of a standard solution of each compound, according to equation (10):

$$C = \frac{d \cdot C_{O2} \cdot V}{do \cdot 2 \cdot V_s} \tag{10}$$

where

C: concentration of the compound determined (μmol/ml)

d: DO construction for the compound determined (cm)

do: DO consumption for air saturated water (cm)

$C_{O2}$: concentration of oxygen in air saturated water (μmol/ml) (0.214 μmol/ml at 37° C.)

2: oxygen equivalent

V: volume of reaction cell (μl)

Vs: volume of sample solution ($S_1$, $S_2$) (μl).

The above procedures may be readily automated by providing a sequencer, a sampler, an injection pump and the like. Calculation of the IMP, HxR and Hx ratios may easily be automatically displayed and recorded by use of a computer such as a microcomputer.

EXAMPLE 1

Preparation of Sample:

To 4 g samples of mackerel and flatfish was added 50 ml of 10% perchloric acid (PCA) solution which were homogenized and centrifuged at 3000 rpm for 10 minutes. The resulting supernatant liquid was filtered with a 5A filter paper, 10N KOH was added and neutralized by use of methyl orange as an indicator and centrifuged at 3000 rpm for 5 minutes. The resulting supernatant liquid was filtered and diluted to 100 ml with deionized water for use as a sample.

Analysis Procedure.

Analysis was carried out according to the second method for determining the degree of freshness.

100 $\mu l$ of an extract solution $S_1$, 20 $\mu l$ of AP and 400 $\mu l$ of G.B. were charged into a 2000 $\mu l$ reaction cell and reacted for 3 minutes followed by the addition of P.B. saturated with air at 37° C. and sealed by a stopper. Thereafter, in the same manner, 20 $\mu l$ of XO, 8 $\mu l$ of NP and 100 $\mu l$ of an extract solution $S_2$ were injected into the reaction cell in order to obtain a consumption curve as represented in FIG. 11.

Calculation:

The IMP, HxR and Hx ratios were determined according to equations (7), (8) and (9), respectively. The results thus obtained are shown in Table 2, which shows that these results are consistent with the results obtained by the conventional enzymatic method as conducted in the Tokai Regional Fisheries Research Laboratory, Marine Product Utilization Division, Fisheries Agency, Japan using the same samples as in this Example. The same results were also obtained using the first method.

EXAMPLE 2

Preparation of Sample:

The procedures were repeated in the same manner as in Example 1.

Analysis Procedure:

The procedures were repeated in the same manner as in Example 1 to obtain a DO consumption curve (see FIG. 11). In order to determine the concentration, to a 2000 $\mu l$ reaction cell filled with P.B. saturated with air was added 100 $\mu l$ of a solution obtained by adding a trace amount of cobalt chloride to an 0.5M $Na_2SO_3$ solution to obtain a consumption curve of from DO saturation to DO zero and to obtain the consumption rate $d_0$ from the consumption curve.

Calculation:

The IMP, HxR and HX ratios were determined in the same manner as in Example 1. The concentrations of each compound were determined according to the following equation (10)':

$$C_{IMP} = (DO \text{ consumption rate corresponding to } IMP) \quad (10')$$
$$\times (DO \text{ concentration per ml})$$
$$\div (O_2 \text{ equivalent}) \times (\text{rate of dilution on reaction})$$
$$= (d_3 - d_2) \frac{0.214 \, (\mu \text{ mol/ml})}{d_0} \times \frac{1}{2}$$
$$\times \frac{2000 \, (\mu l)}{100 \, (\mu l)}$$

This experiment was carried out at $d_0 = 15.2$ cm, $C_{O2} = 0.214$ $\mu l$ mol/ml, V=2000 $\mu l$ and Vs=100 $\mu l$.

TABLE 2

Comparison of the Method of the Present Invention and the Enzymatic Method

| | Storage term | | | | | |
|---|---|---|---|---|---|---|
| | 0 (zero) day | | 3 days | | 6 days | |
| Samples | Method of the present invention | Conventional enzymatic method | Method of the present invention | Conventional enzymatic method | Method of the present invention | Conventional enzymatic method |
| Mackerel | | | | | | |
| IMP ratio (%) | 68.5 | 72.9 | 51.4 | 51.0 | 25.7 | 35.8 |
| HxR ratio (%) | 20.1 | 22.4 | 44.8 | 41.8 | 65.7 | 53.4 |
| Hx ratio (%) | 2.4 | 4.7 | 3.8 | 7.2 | 8.6 | 10.8 |
| Flatfish | | | | | | |
| IMP ratio (%) | 69.1 | 69.1 | 36.4 | 34.0 | 0 | 16.1 |
| HxR ratio (%) | 0 | 0.3 | 0 | 0 | 0 | 0 |
| Hx ratio (%) | 30.9 | 30.6 | 63.6 | 66.0 | 100.0 | 83.9 |

The concentrations CHxR and CHx for HxR and Hx respectively, were determined by replacing $(d_3-d_1)$ in equation (10)' with $(d_2-d_1)$ and $(d_1)$, respectively. The results thus obtained are shown in Table 3.

TABLE 3

Degree of Freshness and Concentration of Each Compound $d_0 = 15.2$

| | Length of DO consumption (cm) | | | Degree of freshness (do) | | | Concentration (μmol/ml) | | | |
|---|---|---|---|---|---|---|---|---|---|---|
| Sample | $d_1$ | $d_2$ | $d_3$ | IMP ratio | HxR ratio | Hx ratio | $C_{IMP}$ | $C_{HxR}$ | $C_{Hx}$ | $C_{IMP} + C_{HxR} + C_{Hx}$ |
| Horse mackerel | | | | | | | | | | |
| 0 (zero) day | 0.2 | trace | 7.0 | 97.1 | trace | 2.9 | 0.98 | trace | 0.028 | 1.008 |
| 4 days | 0.7 | 3.3 | 8.5 | 61.3 | 30.5 | 8.2 | 0.73 | 0.36 | 0.098 | 1.188 |
| Flatfish | | | | | | | | | | |
| 0 (zero) day | 0.7 | 0.4 | 6.6 | 89.4 | — | 10.6 | 0.86 | — | 0.098 | 0.958 |

TABLE 3-continued

Degree of Freshness and Concentration of Each Compound $d_o = 15.2$

| Sample | Length of DO consumption (cm) $d_1$ | $d_2$ | $d_3$ | Degree of freshness (do) IMP ratio | HxR ratio | Hx ratio | Concentration (μmol/ml) $C_{IMP}$ | $C_{HxR}$ | $C_{Hx}$ | $C_{IMP} + C_{HxR} + C_{Hx}$ |
|---|---|---|---|---|---|---|---|---|---|---|
| 4 days | 3.7 | 3.4 | 5.5 | 32.7 | — | 67.2 | 0.294 | — | 0.518 | 0.294 |

EXAMPLE 3

Preparation of Sample:

In addition to extraction with PCA, extraction with trichloroacetic acid (TCA) was carried out. To 10 g samples of canned tuna were separately added 25 ml of 10% PCA and 10% TCA which were pulverized thoroughly in a mortar and centrifuged for 10 minutes at 0° C. and 5000 rpm. The resulting supernatant liquids were filtered with a No. 6 filter paper and then neutralized with 10N KOH by using B.T.B. reagent as an indicator. When PCA was used, white precipitates, which were formed, were filtered and the filtrate was diluted to 100 ml with deionized water When TCA was used, the neutralized solution was directly diluted to 100 ml with deionized water.

Analysis Procedure:

The procedures were repeated in the same manner as in Example 2. For comparison, the HPLC method was conducted under the conditions and using the equipment below Samples were subjected to analysis after being filtered through a microfilter.

HLPC Method:

High performance liquid chromatograph.
LC-5A type of Shimadzu Corporation
Column: 25 cm × 4 mm
Filler: Unisil $C_{18}$ Gaschro Kogyo Co., Ltd.) 10 φ
Detector: UV detector (254 mm)
Elutant: 0.01M $(NH_4)_2 HPO_4$
Flow rate: 0.8 ml/min.

Under these conditions, chromatograms of xanthine (X), hypoxanthine (Hx), Inosine (HxR), inosinic acid (IMP) and adenosine monophosphate (AMP), which are not shown, had very sharp peaks.

Calculation:

In the case of the method of the present invention, each compound ratio and concentration was determined in the same manner as in Example 2. In the case of the HPLC method, concentrations of each compound were determined from the ratio of the peak height thereof to that of a standard sample having a known concentration. A comparison of the results of both methods is shown in Table 4.

Table 4 shows that the results of the method of the present invention are consistent with the results obtained by the HPLC method. TCA was shown to be a practical extractant from the fact that a change of the extraction from PCA to TCA had no effect on the IMP and Hx ratios, that, since use of TCA forms no precipitation on neutralization, the filtration procedure can be omitted, and further, that TCA is a safer reagent than PCA.

EXAMPLE 4

Preparation of Sample:

A standard solution with IMP:HxR:Hx=1:1:1 (1 μl mol/each compound) was prepared. Horse mackerel stored in the refrigerator for 4 days similar to that used in Example 2 was used as a fish sample $S_1$.

Figure 13:
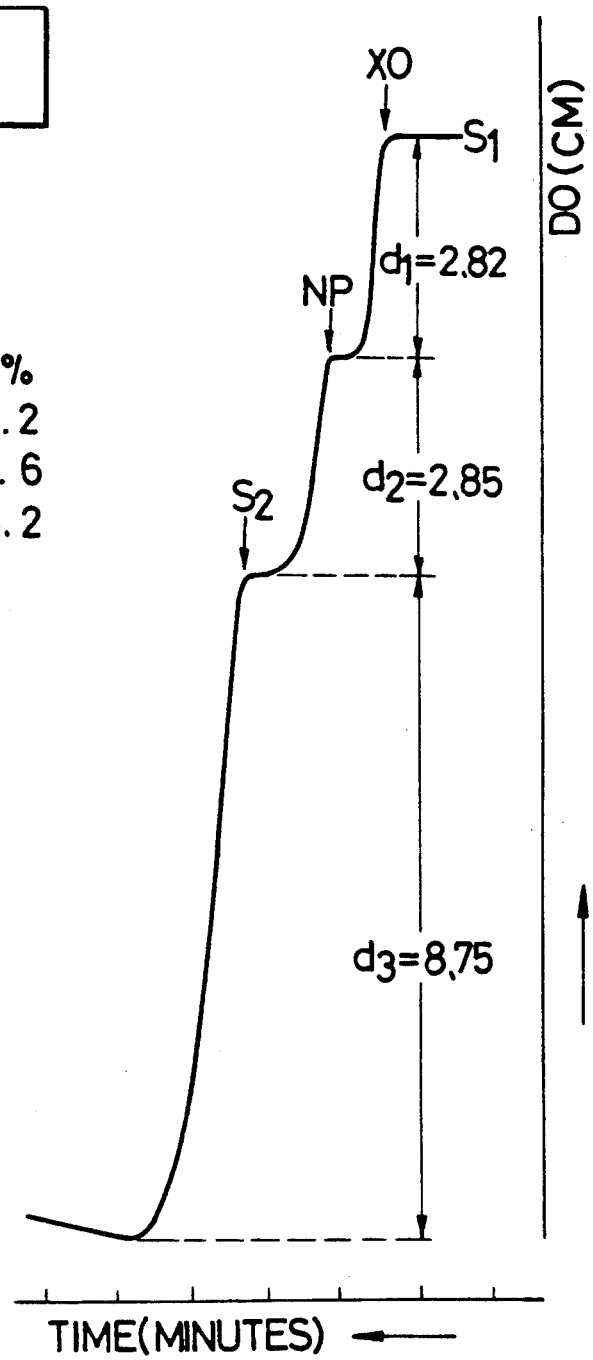
FIG. 13 is a curve showing DO consumption in an extract solution from horse mackerel.

Analysis Procedure:

To a separate vessel was charged 100 μl of the standard solution, 20 μl of AP and 80 μl of G.B. which were subjected to a pre-reaction at 37° C. To a reaction cell sealed according to the third method, 40 μl of the standard solution, 20 μl of XO and 8 μl of NP; and, separately, 80 μl of the standard solution, with which AP had been reacted and which had been diluted twice; were injected in order to obtain a consumption curve with 3 steps. The results thus obtained are shown in FIG. 13. Since the concentration of the extract solution was lower than that of the standard solution, 250 μl of the extract solution, 40 μl of AP and 210 μl of G.B. were charged to effect the pre-reaction. The amount of the sample $S_1$ charged initially was 100 μl.

The horse mackerel sample was also subjected to analysis according to the HPLC method under the conditions shown in Example 3.

Calculation:

According to the third method, the IMP, HxR and Hx ratios are as follows:

$$IMP\ ratio = \frac{d_3 - (d_2 + d_1)}{d_3} \times 100(\%) \qquad (7)'$$

$$HxR\ ratio = \frac{d_2}{d_3} \times 100(\%) \qquad (8)'$$

TABLE 4

Comparison of the Method of the Present Invention and the HPLC Method

| Extractant | Method of analysis | $C_{IMP}$ (μmol/ml) | $C_{HxR}$ (μmol/ml) | $C_{Hx}$ (μmol/ml) | IMP ratio (%) | HxR ratio (%) |
|---|---|---|---|---|---|---|
| PCA | HPLC method | 0.318 | 0.146 | not detected | 68.5 | 31.4 |
| PCA | Method of the present invention | 0.252 | 0.126 | not detected | 66.6 | 33.3 |
| TCA | Method of the present invention | 0.308 | 0.168 | not detected | 64.7 | 35.3 |

-continued $$Hx \text{ ratio} = \frac{d_1}{d_3} \times 100(\%). \quad (9)'$$

Figure 14:
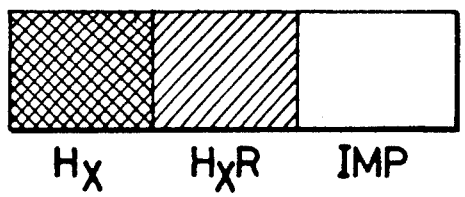
FIG. 14 is a digital and graph representation of the degree of freshness, automatically recorded by an off-line microcomputer.

The DO consumptions $d_1$, $d_2$, and $d_3-(d_2+d_1)$, obtained from FIG. 13, were calculated by microcomputer as shown in FIG. 14.

The concentration of IMP was obtained according to equation (10)' below for the standard solution.

$$C_{IMP} = (d_3 - d_2 - d_1) \times \frac{0.214}{d_0} \times \frac{1}{2} \times \frac{2000}{40} (\mu \text{ mol/ml}) \quad (10)'$$

In the case of the extract solution, the rate of dilution was 2000/100=20. $C_{HxR}$ and $C_{Hx}$ were determined by replacing $(d_3-d_2-d_1)$ in equation (10)' with $d_2$ and $d_1$ respectively. The results thus obtained are shown in Table 5.

TABLE 5

Comparison of the Second and Third Methods of the Present Invention and the HLPC Method

| Sample | Method of analysis | IMP ratio (%) | HxR ratio (%) | Hx ratio (%) | $C_{IMP}$ (μmol/ml) | $C_{HxR}$ (μmol/ml) | $C_{Hx}$ (μmol/ml) |
|---|---|---|---|---|---|---|---|
| Standard solution | The third method of the present invention | 31.9 | 34.5 | 33.6 | 0.98 | 1.06 | 1.03 |
| Horse mackerel 4 days | The third method of the present invention | 58.0 | 33.9 | 8.0 | 0.65 | 0.38 | 0.09 |
| | The second method of the present invention (see Table 3) | 61.3 | 30.5 | 8.2 | 0.73 | 0.36 | 0.10 |
| | HPLC method | 60.2 | 31.0 | 8.8 | 0.68 | 0.35 | 0.10 |

As is apparent from Table 5, the results obtained according to the third method were consistent with the results obtained according to the second method and to the HPLC method.

EXAMPLE 5

Preparation of Sample:

The standard solution with IMP:HxR:Hx=1:1:1 as prepared in Example 4 was used.

Analysis Procedure:

Analysis was carried out according to the second method. The procedure of Example 1 was repeated except that the amount of the sample was changed from 100 μl to 40 μl. The change in the output of the DO sensor was sent to a recorder through an amplifier, and then to an on-line computer via an A/D converter (not shown).

Figure 15:
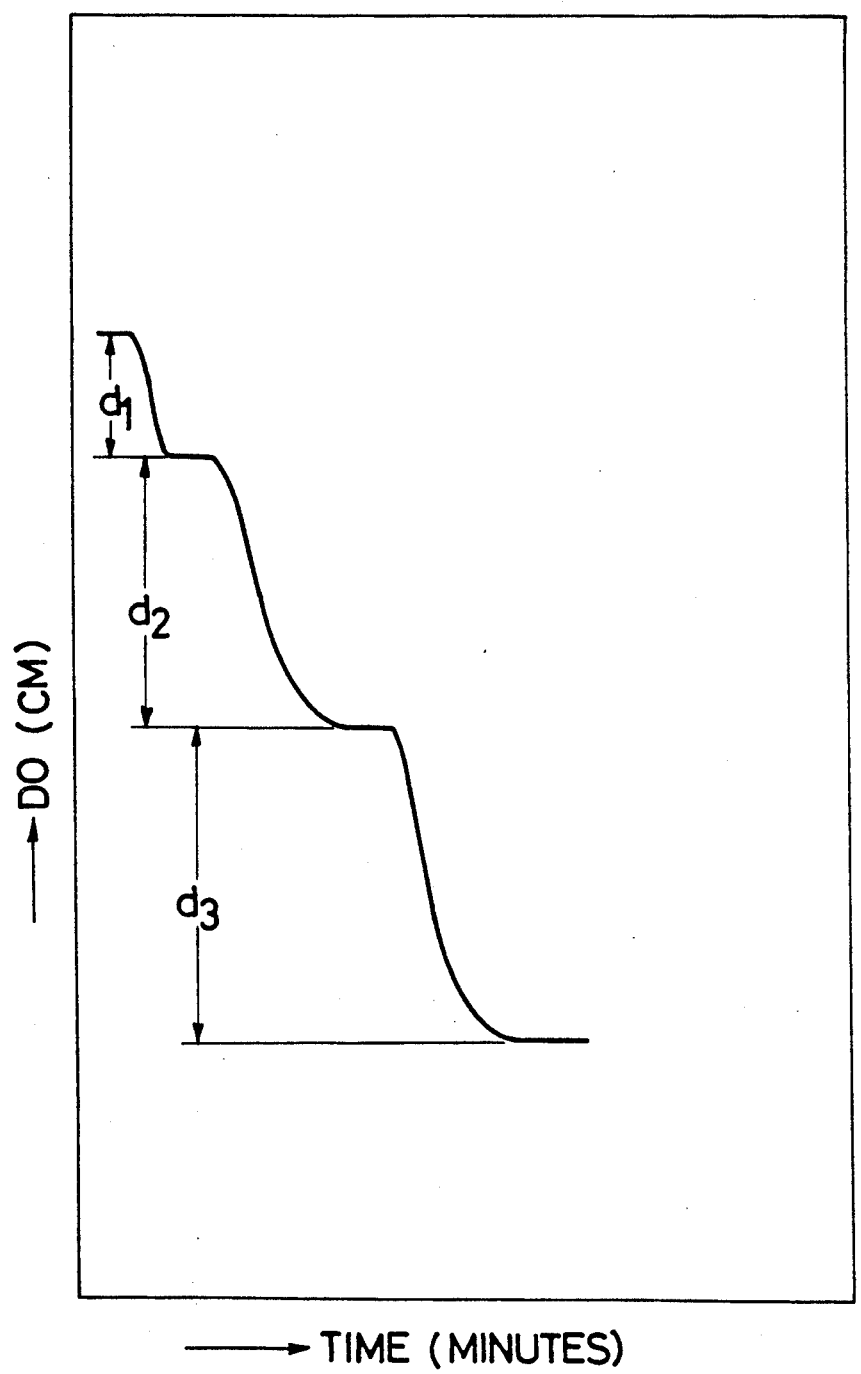
FIG. 15 is a curve showing DO consumption, automatically recorded by an on-line microcomputer.

As the reaction proceeded, the DO change was displayed as shown as a DO consumption curve as in FIG. 15. The curve thus obtained is the same as that obtained by a recorder. In other words, operations of equations (7), (8) and (9) were carried out automatically by a computer.

EXAMPLE 6

Preparation of Sample:

To 10 g samples of chicken wing and breast stored in a refrigerator was added 40 ml of 10% TCA which were homogenized, centrifuged at 6000 rpm for 10 minutes, neutralized, and diluted to 50 ml.

Analysis Procedure:

Analysis was carried out according to the third method. 350 μl of an extract solution $S_2$, 20 μl of AP, and 330 μl of G.B. were subjected to reaction in a separate vessel. 100 μl of an extract solution $S_1$, 20 μl of XO and 80 μl of NP were subjected to pre-reaction, and 200 μl of the resulting extract solution (corresponding to 100 μl of $S_1$) was subjected to reaction in the same manner to obtain a DO consumption curve.

Calculation:

The procedure of Example 4 was repeated to determine the IMP, HxR and Hx ratios, $C_{IMP}$, $C_{HxR}$, and $C_{Hx}$ at a dilution rate of 2000/100=20 and $d_0=16.1$ cm. The results thus obtained are shown in Table 6. The analysis took 3 minutes.

TABLE 6

Analysis of the Third Method

| Sample | Degree of freshness (do) | | | Concentration of compounds (μmol/ml) | | | |
|---|---|---|---|---|---|---|---|
| | IMP ratio | HxR ratio | Hx ratio | $C_{IMP}$ | $C_{HxR}$ | $C_{Hx}$ | Total |
| Chicken wing (2 days) | 64.6 | 28.9 | 6.5 | 0.615 | 0.274 | 0.062 | 0.951 |
| Chicken breast (2 days) | 72.6 | 20.2 | 7.2 | 0.771 | 0.214 | 0.077 | 1.06 |
| Chicken breast (4 days) | 45.8 | 34.8 | 19.4 | 0.374 | 0.284 | 0.158 | 0.816 |

As the above description and examples clearly show, the present invention makes possible a rapid analysis of ATP decomposition products in a few minutes by the application of a simple, small DO measuring instrument, while the prior art normally takes several hours for the analysis of each compound of the ATP decomposition products, and requires the use of a liquid chromatograph or ultraviolet spectrophotometer for measurement. Further, the method of the present invention is more economical in that it requires only a very small amount of enzymes to detect the compounds with a DO sensor.

The degree of freshness can be calculated directly from the ratio of recorded DO consumption, resulting not only in convenient manual calculation but also in easy automatic analysis by computer. With the above advantages, the method of the present invention for determining the degree of freshness can be readily carried out on site where perishable foodstuffs are produced and sold as well as in a laboratory with special equipment and skilled personnel. As a result, the method of the present invention can support the food industry, leads to improvements in food sanitation and provides greater protection for consumers among other benefits.

What is claimed is:

1. Apparatus for determining the degree of freshness of raw, frozen and processed perishable foodstuffs by measuring a consumption of dissolved oxygen by the foodstuffs during a predetermined time period sufficient for the consumption to occur, comprising:

a temperature controlled reaction cell having an opening;

a removable stopper hermetically sealing the opening, said stopper having an open, a capillary extending therethrough for liquid injection; and an oxygen sensor mounted for measuring a value of dissolved oxygen in said cell, wherein said capillary has a minimum diameter of substantially 1 millimeter which is sufficiently small so that oxygen diffusion through said capillary during said time period is substantially zero, whereby measurements by said oxygen sensor are not affected.

* * * * *